(12) United States Patent
Watanabe et al.

(10) Patent No.: US 7,879,779 B2
(45) Date of Patent: Feb. 1, 2011

(54) OIL-CLEANSING COMPOSITION

(75) Inventors: Kei Watanabe, Yokohama (JP); Akira Matsuo, Yokohama (JP); Hiroki Inoue, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 764 days.

(21) Appl. No.: 10/585,146

(22) PCT Filed: Jan. 11, 2005

(86) PCT No.: PCT/JP2005/000176

§ 371 (c)(1),
(2), (4) Date: Jun. 30, 2006

(87) PCT Pub. No.: WO2005/079729

PCT Pub. Date: Sep. 1, 2005

(65) Prior Publication Data

US 2008/0293603 A1    Nov. 27, 2008

(30) Foreign Application Priority Data

Jan. 9, 2004    (JP) .............................. 2004-004055

(51) Int. Cl.
*A61K 7/02*    (2006.01)
(52) U.S. Cl. ................. 510/130; 510/407; 510/417; 510/505
(58) Field of Classification Search ................. None
See application file for complete search history.

(56) References Cited

U.S. PATENT DOCUMENTS 5,015,469 A * 5/1991 Yoneyama et al. ............ 424/59

FOREIGN PATENT DOCUMENTS

EP    1488775    * 10/2003

OTHER PUBLICATIONS

Japanese Patent Abstract Publication No. 2000-327529 published Nov. 28, 2000, one page.
Japanese Patent Abstract Publication No. 06-016524 published Jan. 25, 1994, one page.
Japanese Patent Abstract Publication No. 2001-270809 published Oct. 2, 2001, one page.

* cited by examiner

*Primary Examiner*—Necholus Ogden, Jr.
(74) *Attorney, Agent, or Firm*—Rankin, Hill & Clark LLP

(57) ABSTRACT

The objective of this invention is to provide an oil-based cleansing composition which retains high performance capability for cleansing, is free from the occurrence of cloudiness in the appearance and does not cause the reduction of the performance capability for massaging, even when water is interfused therein, and further is reduced in the irritation to an eye and is of good safety.

An oil-based cleansing composition of this invention is characterized in that comprising (A) a nonionic surfactant having a HLB of 6 to 14, and (B) an oil component, and said oil-based cleansing composition satisfies the following conditions (1) and (2):

(1) the amount of water in the composition is less than 5% by mass, and
(2) a micellar aqueous solution phase or a bicontinuous microemulsion phase is formed when said oil-based cleansing composition and water are mixed in the ratio of 4:6.

11 Claims, 1 Drawing Sheet

OIL-CLEANSING COMPOSITION

RELATED APPLICATIONS

This application claims priority to the Japanese Patent Application 2004-004055 dated on Jan. 9, 2004 and is hereby incorporated with reference for all purposes.

BACKGROUND OF THE INVENTION

1. Field of the Invention

The present invention relates to an oil-based cleansing composition, and in particular, relates to the prevention of transparency decrease due to interfused water.

2. Prior Art

Cleansing compositions can be broadly classified to water-based cleansing compositions and oil-based cleansing compositions. As water-based cleansing compositions, there are lotion type compositions which consist of an ethanol aqueous solution of a surfactant and aqueous gel-type compositions, in which the surfactant is thickened with a polymer. As for the oil-based cleansing compositions, there are cream type compositions, which can achieve a cleansing function, during massage, by the inversion of an O/W emulsion, and oil type compositions (cleansing oil) that consists of an oil solution of a surfactant.

Among these, the oil type composition is known to have a high cleansing effect. In recent years, the favorable makeup is of the type, with which the secondary adhesion of foundation or lipstick is prevented, and of the type, in which high-polymer silicone is contained, such as mascara. Thus, the demand of the oil type composition in the market is becoming very high.

The oil type composition consists of a nonionic surfactant, an oil component, and a small amount of water, and they forms a reverse micellar solution, in which the surfactant forms aggregates in the oil component by arranging hydrophilic groups along the inner side. Water is solubilized in the core of the micelle where the hydrophilic groups gather, and the prepared 1-phase solution is completely transparent.

In the ability to take water completely in a transparent state, namely, in the solubilizing power, the oil type composition has a limitation, because of its microstructure. When water is interfused beyond the solubilizing power, the coexistence with another phase (two phase state) takes place, that is, a water-in-oil type or an oil-in-water type emulsion is typically formed. When the size of the internal phase particles becomes more than a certain size, the solution turns into white turbidity, as a whole, because of scattered light due to the difference in the refractive indexes of the two phases. In this case, the preferable cleansing performance and smoothness of massaging may not be achieved depending upon the coexisting phase. In addition, white turbidity is undesirable because it strongly suggests decreased the performance to consumers.

Thus, an oil-based cleansing compositions cannot be used in a bath with wet hands; in addition, it cannot be used on a wet face after shampooing hair, thus restricting the usage.

It is described that a cleanser that easily adapts to makeup even if the skin is wet (Japanese Patent Publication 2000-327529). This was achieved by simultaneously using a polyglyceryl fatty acid ester that has the HLB of not less than 10 and a polyhydric alcohol that is trihydric or more. However, the white turbidity could not be prevented by this method, and the smoothness of massaging was often not sufficient.

It is described that cleansing compositions with high cleansing performance, even when used with wet hands (Japanese Patent Publication Hei 6-16524, and Japanese Patent Publication 2001-270809). They were prepared by combining a nonionic surfactant and an amphoteric surfactant or by combining a nonionic surfactant and a glyceryl ether derivative. However, the smoothness of massaging and the prevention of white turbidity were not consistently satisfactory.

An objective of the present invention is to provide a safe oil-based cleansing composition that has little eye irritation and has high cleansing performance, no white turbidity, and no reduced smoothness of massaging even when water is interfused.

SUMMARY OF THE INVENTION

This invention is an oil-based cleansing composition comprising (A) a nonionic surfactant having a HLB of 6 to 14, and (B) an oil component, and said oil-based cleansing composition satisfies the following conditions (1) and (2):

(1) the amount of water in the composition is less than 5% by mass, and (2) a micellar aqueous solution phase or a bicontinuous microemulsion phase is formed when said oil-based cleansing composition and water are mixed in the ratio of 4:6.

As the above-mentioned oil-based cleansing composition, it is preferable that the IOB of (B) said oil component is 0.02 to 0.07, and the mass ratio of component (A) and component (B) is 1:4 to 2:1.

As the above-mentioned oil-based cleansing composition, it is preferable that the alkyl chain length in (A) said nonionic surfactant is not less than 16 on the average.

As the above-mentioned oil-based cleansing composition, it is preferable that (B) said oil component contains not less than 80% of hydrocarbon oil and/or ester oil.

Also, it is preferable that (B) said oil component further contains 1 to 10% of silicone oil.

As the above-mentioned oil-based cleansing composition, it is preferable that (C) a liquid fatty acid or a liquid alcohol with the alkyl chain length of not less than 16 is further contained.

As the above-mentioned oil-based cleansing composition, it is preferable that the mass ratio of component (C) and component (A) is in the range of 1:40 to 1:3.

As the above-mentioned oil-based cleansing composition, it is preferable that the below-described condition (3) is satisfied in addition to conditions (1) and (2): (3) the viscosity measured with a B-type viscometer is not more than 10000 mPa·s when said oil-based cleansing composition and water is mixed in the mass ratio of 7:3.

In order to prevent the white turbidity, which is caused by the interfusion of water to an oil-based cleansing composition, the suppression of light scattering can be considered. The suppression of light scattering can be achieved by reducing the refractive index difference between the water phase and the oil phase or by reducing the size of the internal phase particles to the wavelength range of visible light. In the oil-based cleansing composition, the water phase to be added is usually tap water; thus, the adjustment of the refractive index is difficult. It is also difficult to reduce the emulsion particle size to less than a few hundred nm by finger mixing.

In these circumstances, the present inventors have adjusted, in advance, a nonionic surfactant and an oil component so that either a bicontinuous microemulsion phase or a micellar aqueous solution, which is a low-viscosity 1-phase, is formed even when water is added to the oil-based cleansing composition.

According to the present invention, a safe oil-based cleansing composition that has little eye irritation and has high cleansing performance, no white turbidity, and no reduced smoothness of massaging, even when water is interfused, can be prepared.

DETAILED DESCRIPTION OF THE PREFERRED EMBODIMENT

Figure 1:
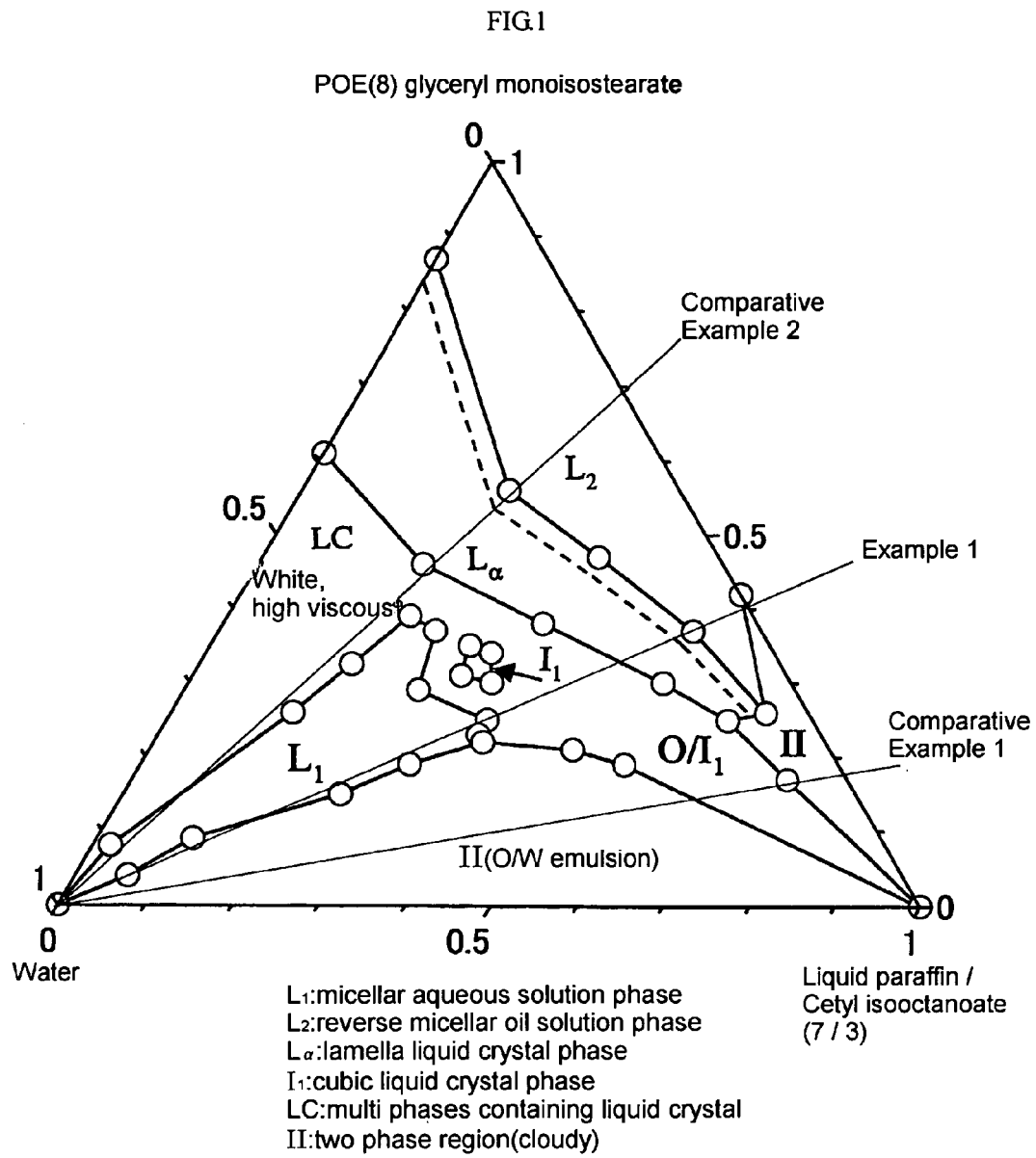
FIG. 1 shows a pseudo ternary phase diagram (water/surfactant/oil component), in which the components in Example 1 and Comparative Examples 1 and 2 are used.

Preferable embodiments of the present invention are explained below.

Nonionic Surfactant

A nonionic surfactant (A) used in the present invention has no ionic charge in aqueous solution. As for the hydrophobic group, the alkyl type and dimethylsilicone type are known. Specific examples of the former include, for example, glyceryl fatty acid esters, ethylene oxide derivatives of glyceryl fatty acid esters, polyglyceryl fatty acid esters, propylene glycol fatty acid esters, ethylene oxide derivatives of propylene glycol fatty acid esters, polyethylene glycol fatty acid esters, polyethylene glycol alkyl ethers, polyethylene glycol alkyl phenyl ethers, polyethylene glycol castor oil derivatives, and polyethylene glycol hydrogenated castor oil derivatives. Examples of the latter include polyether-modified silicone and polyglycerin-modified silicone. A preferable hydrophobic group is an alkyl type.

The HLB of the nonionic surfactant in the present invention is preferably 6 to 14, and more preferably 8 to 10. When the HLB is 7, the solubility of the surfactant into water and the solubility of the surfactant into oil are generally balanced. That is, a desirable surfactant in the present invention has intermediate solubility in oil and water, or it is slightly hydrophilic. If the HLB is less than 6, good rinsing capability of the cleanser cannot be achieved. If the HLB is more than 14, an oil-based cleansing composition cannot be prepared because the solubility of the surfactant into oil is significantly reduced. If the HLB is 8 to 10, there is an advantage in that the selection of an oil component is easy. It is preferable that the nonionic surfactant in the present invention is liquid at ordinary temperature.

The nonionic surfactant used in the present invention preferably has an alkyl chain length of not less than 16 when an alkyl type is used. If the chain length of the alkyl group is short, the surfactant has a tendency to cause higher eye irritation.

The lipophilic group of the (A) component surfactant is preferably of a branched or unsaturated alkyl type, more preferably an isostearyl group or oleyl group, and most preferably an isostearyl group. The preferable (A) component surfactant in the present invention is POE glyceryl isostearate.

The blending amount of component (A) should be 15 to 65% by mass, and preferably 25 to 50% by mass. If the blending amount is equal to or less than this, the prevention of the white turbidity will not be satisfactory. If the amount is equal to or more than this, an undesirable sticky feeling is caused.

Oil Component

As the (B) oil component, one or more kinds of oil component that is generally used in cosmetics can be selected within the range that the stability is not jeopardized. In particular, when a nonionic surfactant with the HLB of 8 to 10 is selected, one or more kinds of oil component with the average IOB of 0.02 to 0.07 can be selected. The preferable oil component is a hydrocarbon oil or polar oil. If a small amount of silicone oil (1 to 20% by mass with respect to the oil component) is mixed with these oils, the cleansing performance can be improved. The (C) component described later is not included in the (B) oil component.

Examples of hydrocarbon oils include liquid paraffin, squalane, squalene, paraffin, isoparaffin, and ceresin.

It is preferable to blend a small amount of a polar oil component within the range that the stability is not jeopardized. As for the polar oils, there are liquid fats and ester oils. Examples of liquid fats include linseed oil, camellia oil, macadamia nut oil, corn oil, mink oil, olive oil, avocado oil, camellia sasanqua oil, castor oil, safflower oil, jojoba oil, sunflower oil, almond oil, rapeseed oil, sesame oil, soybean oil, peanut oil, triglycerides, glyceryl trioctanoate, and glyceryl triisopalmitate. Examples of ester oils include cetyl octanoate, hexyl laurate, isopropyl myristate, octyl palmitate, isocetyl stearate, isopropyl isostearate, octyl isopalmitate, isodecyl oleate, glyceryl tri-2-ethylhexanoate, pentaerythrityl tetra-2-ethylhexanoate, 2-ethylhexyl succinate, and diethyl sebacate.

Examples of silicone oils, which are added to improve the cleansing performance, include chain silicones such as dimethylpolysiloxane, methylphenylpolysiloxane, and methyl hydrogen polysiloxane; and cyclic silicones such as octamethylcyclotetrasiloxane, decamethylcyclopentasiloxane, and dodecamethylcyclohexasiloxane.

It is preferable to blend component (A) and component (B) so that the mass ratio of (A):(B) is 1:4 to 2:1. In particular, when the sum of the hydrocarbon oil and ester oil in the oil component is not less than 80% by mass, it is desirable that (A):(B) is 1:3 to 2:1. If component (A) is blended more than this, a sticky feeling may be caused. In addition, the smoothness of massaging, which is expected when water is interfused, may not be achieved. If the blending amount is equal or less than this, white turbidity may be caused when water is interfused.

The amount of blended water in the present invention is less than 5% by mass, and water need not be blended. If the amount of blended water is not less than 5% by mass, the transparency may not be satisfactory as a cleansing composition.

Liquid Fatty Acid and Liquid Alcohol

A liquid fatty acid or a liquid alcohol (C), which is used in the present invention, with an alkyl chain length of more than 15 is liquid because the alkyl group is branched or contains unsaturated bonds. Examples of liquid fatty acids include isostearic acid and oleic acid, and examples of liquid alcohols include isostearyl alcohol and oleyl alcohol. Isostearic acid and isostearyl alcohol are most preferable.

It is preferable to blend component (C) and component (A) so that the mass ratio of (C):(A) is 1:40 to 1:3. If component (C) is blended more than this range, a sticky heavy oil feeling is generated. If component (C) is blended less than this range, a desired prevention effect of the white turbidity, which is caused when water is interfused, may decrease. It is preferable that the mass ratio of component (C) and component (B) is in the range of 1:30 to 1:4.

As described in condition (2) of the present invention, when the composition and water are mixed in the ratio of 4:6, it is necessary that a micellar aqueous solution phase or a bicontinuous microemulsion phase is generated. In addition, as described in condition (3), when the composition and water are mixed in the ratio of 7:3, it is preferable that the viscosity measured by a B-type viscometer is not more than 10000 mPa·s (rotation: 6 rpm, temperature: 25° C., and measured with rotor No. 3).

A mixture of oil and water takes one of the following modes.
(1) Micellar aqueous solution
(2) Reverse micellar oil solution
(3) Water-in-oil type emulsion
(4) Oil-in-water type emulsion
(5) Bicontinuous microemulsion
(6) Liquid crystal Among these, the emulsion is very common, and most of cosmetics are classified to emulsion. As represented by cream and milky lotion, most of them have white turbidity. In the case of liquid crystals, a liquid crystal without much light scattering and without the white turbidity can be prepared; however, significant thickening is often caused because of its structure.

Thus, the present inventors have developed an oil-based cleansing composition in which a nonionic surfactant and an oil component are adjusted in advance so that a micellar aqueous solution or a bicontinuous microemulsion is formed when water is added.

In the following section, methods for the investigation of the phase change, which takes place during the water interfusion, are described.

It is widely known that a ternary diagram is utilized in order to understand a three component system formed of an oil component, water, and a surfactant. At each corner of the ternary diagram, three components are positioned, and each position indicates that the composition of the component is 100% by mass. When territories of the phases obtained by mixing the components are diagrammatically shown on the ternary diagram, the diagram is called a ternary phase diagram. On the ternary phase diagram, all mixing ratios of respective components are contained. When a mixture is positioned at a corner based on their properties, the diagram is a pseudoternary phase diagram. For example, when a mixture of water and ethanol at a certain constant concentration is positioned at a corner as the aqueous component, a pseudoternary phase diagram can be constructed for four components, namely, water, ethanol, surfactant, and oil.

The oil-based cleansing composition in the present invention consists of a nonionic surfactant, an oil component (one or more kinds), and a ternary phase diagram can be constructed when water is added. When a liquid alcohol or liquid fatty acid is also contained, the surfactant and liquid alcohol or the surfactant and liquid fatty acid can be regarded as one component. When more than one kind of oil is used, they also can be regarded as one component. In these cases, a pseudo ternary phase diagram can be constructed.

The composition of the present invention is prepared by mixing an oil component into a surfactant or mixing an oil component into a mixture of a surfactant and a liquid fatty acid and then adding a small amount of water as necessary. Therefore, in the pseudo ternary phase diagram, it is located at a point that is slightly deviated to the direction of the water corner from one point on the axis connecting the corner of the surfactant, which contains the liquid fatty acid, and the oil corner (when water is not contained, it is located at a point on the axis connecting the surfactant corner and the oil corner). A change caused by the water interfusion corresponds to the compositional change from this point to the direction of the water corner.

A micellar aqueous solution phase and a bicontinuous microemulsion phase, which are formed during the water interfusion under condition (2) of the present invention, have the following characteristics, and their differentiation is possible. Both the micellar aqueous solution phase and the bicontinuous microemulsion phase are optically isotropic, transparent, low-viscosity solutions. The only other isotropic, transparent, low-viscosity solution that can be obtained in surfactant systems is a reverse micellar oil solution. The methods to differentiate these are described below.

In the micellar aqueous solution phase, water is continuous, and globular or cylindrical associations are dispersed with lipophilic groups facing inside. The size of the aggregate is ca. 100 nm at the largest, and the micellar aqueous solution shows optically isotropic, from clear to slightly blue, translucent appearance. The composition is obtained by adding a surfactant and an oil component to water. Because the solubilization of the oil component increases with an increase the amount of the surfactant, it is often located, on the phase diagram, in the region from the water corner to the center of the phase diagram.

On the other hand, the association number of surfactant increases in the bicontinuous microemulsion phase, and the infinite association takes place. As a result, the solubilizing power for water and oil drastically improves, and both water and oil form continuous channels. The determination of the bicontinuous microemulsion phase can be achieved by the appearance, construction of a phase equilibrium diagram, electrical conductivity measurement, self-diffusion coefficient measurement by NMR, and electron microscopic observation of replicas prepared by the freeze-fracture method.

The bicontinuous microemulsion is, by appearance, a transparent, low-viscosity 1-phase, and it is optically isotropic. It is possible to distinguish this phase from the optically anisotropic liquid crystal phase by confirming the absence of light transmission by holding the sample between two polarizers with a 90 degree phase difference. The distinction of the bicontinuous microemulsion phase from the micellar aqueous solution and reverse micellar oil solution, which are other isotropic 1-phases, can be effectively achieved by the following method.

On the phase equilibrium diagram of a three-component system consisting of water/oil/surfactant (including cosurfactant), the identification of a bicontinuous microemulsion phase is possible based on the following characteristics. It is an isotropic transparent, low-viscosity 1-phase region that is not continuous from either the water corner or the oil corner. However, these characteristics vary depending upon the constituting system. It is known that the electrical conductivity of a bicontinuous microemulsion is ca. ⅔ of that of the micellar aqueous solution phase of the same system. The self-diffusion coefficient measurement with NMR is a method described in detail by Lindman et al. in J. Colloid Interface Sci. 1981, 83, 569. In the electron microscopic observation of a bicontinuous microemulsion that is prepared by the freeze-fracture method, it is possible to observe an image in which both water and oil are continuous. It is easy to differentiate this image from the globular aggregate image observed for the continuous micellar solution phase of water or that of oil. This method is described in detail by Imae et al. in the literature, Colloid Polym. Sci. 1994, 272, 604. On the phase diagram, it is often formed in the ratio of water and oil of ca. 7:3 to 3:7 centering at ca. 1:1. It is also often obtained as a continuous region from the micellar aqueous solution. In this case, it is a continuous region from the water corner.

If the mass ratio of component (A), the nonionic surfactant, and component (B), the oil component, is 1:4 to 2:1, and the ratio of the composition and water is 4:6, the ratio of water and oil will be 3.2:6 to 1.3:6. That is, the water content in the total composition will be 65 to 82% by mass, and the optically isotropic, transparent, low-viscosity solution can be a micellar aqueous solution or a bicontinuous microemulsion.

If a micellar aqueous solution or a bicontinuous microemulsion is not generated when the cleansing composition of the present invention is mixed with water in the ratio of 4:6, desired characteristics of the present invention cannot be realized. The HLB of the surfactant used in the present invention is 6 to 14, and it is hydrophilic. Therefore, on the phase diagram, a continuous region of a bicontinuous microemulsion phase is obtained, in most cases, from the water corner and through a micellar aqueous solution region.

In the region where the surfactant concentration is lower than this, an O/W emulsion phase with complete white turbidity is formed judging from the HLB. In the O/W emulsion phase, surfactant forms micelles in water, and the oil is dispersed in an approximate size of a few μm. As a result, the light of the entire wavelength is scattered; thus, white color is generated. In addition, a desired cleansing effect cannot be achieved because the continuous external phase is water.

In the region where the surfactant concentration is higher than this, liquid crystals are often formed. In the region including liquid crystal, white turbidity as well as high viscosity is generated; thus, the smoothness of massaging, that is desired in the present invention cannot be achieved.

Although the following case does not come under the present invention, there is a case in that a micellar aqueous solution region is extremely small and located only in the vicinity region of the water corner. In this case, a transparent state cannot be obtained even if the composition of the present invention is mixed with water in the ratio of 4:6. This phenomenon often takes place when the solubilizing power of the surfactant is not sufficient, or the oil has a structure that is hard to be solubilized. Specific cases are as follows: a case in which the oil belongs to a silicone series whereas the surfactant belongs to an alkyl series, its opposite case, and a case in which the molecular weight of the oil is too large.

EXAMPLES

In the sections below, the present invention will be described in further detail with specific examples. However, the present invention is not limited by these examples. The composition is expressed with % by mass.

The evaluation method of examples will be explained before describing examples.

(1) Criteria for the Phase State when Water is Interfused

○: It practically belongs to a 1-phase of a micellar aqueous solution phase or bicontinuous microemulsion phase.

x: It belongs to other phases.

(2) Transparency Test when Water is Interfused

The measurement of UV absorbance at the wavelength of 600 nm was conducted after the composition was mixed with water in the ratio of 4:6.

(Criteria for the Transparency)

○: The absorbance is less than 1.

Δ: The absorbance is not less than 1 and less than 4.

x: The absorbance is not less than 4.

(3) Viscosity Measurement when Water is Interfused

The composition was mixed with water in the ratio of 4:6; then the viscosity was measured with Rotor No. 3 of a B-type viscometer at 6 rpm at 25° C.

(4) Cleansing Performance when Water is Interfused

Ten professional panel members with eye makeup were requested to use the cleansing compositions, and they were asked about the cleansing effect after the use.

(Criteria for the Cleansing Performance)

○: More than 6 members out of 10 answered that the cleansing performance was high.

Δ: 3 to 6 members out of 10 answered that the cleansing performance was high.

x: Less than 3 members out of 10 answered that the cleansing performance was high.

(5) Evaluation Method of Eye Irritation

Ten professional panel members with eye makeup were requested to use the cleansing compositions without being told the purpose of the test, and they were asked about the presence or absence of eye irritation after the use.

(Criteria for the Eye Irritation)

○: Less than 2 members out of 10 reported eye irritation.

Δ: 2 to 3 members out of 10 reported eye irritation.

x: More than 3 members out of 10 reported eye irritation.

Example 1 and Comparative Examples 1 and 2

Cleansing compositions were prepared according to the formulations shown in Table 1. A pseudoternary phase diagram (water-surfactant-oil component) for the components used in Example 1 and Comparative Examples 1 and 2 are shown in FIG. 1. From the phase equilibrium diagram, it is shown that a micellar aqueous solution ($L_1$) is formed in Example 1 when water is interfused and that other phases are formed in Comparative Examples 1 and 2.

These compositions were evaluated based on the above-described criteria, and the results are also shown in Table 1.

TABLE 1

| Component | Exam. 1 | Comparative Exam. 1 | Comparative Exam. 2 |
|---|---|---|---|
| Ion exchange water | 1 | 1 | 1 |
| POE(8) glyceryl monoisostearate (HLB; 9) | 40 | 18 | 70 |
| Liquid paraffin | 41.3 | 56.7 | 34.3 |
| Cetyl isooctanoate | 17.7 | 24.3 | 14.7 |
| Phase state when water is interfused | ○ | x (W/O emulsion) | x (liquid crystal) |
| Transparency test when water is interfused | ○ | x | x |
| Viscosity (mPa·s) when water is interfused | 1500 | 350 | 10800 |
| Cleansing performance when water is interfused | ○ | x | Δ |
| Eye irritation | ○ | ○ | ○ |

In the examples shown in Table 1 and FIG. 1, the composition enters into the $L_1$ region by the addition of water if the ratio of the (A) nonionic surfactant and the (B) oil component is in X region. The X region is understood to be the region of POE(8) glyceryl monoisostearate:(liquid paraffin+cetyl isooctanoate)=1:3 to 2:1.

The $L_1$ region slightly moves by the adjustment of the IOB of the oil component; thus, it was found that a preferable oil-based cleansing composition could be obtained when the ratio of the nonionic surfactant and the oil component is 1:4 to 2:1.

On the other hand, in order to form a bicontinuous microemulsion in the oil-water mixed system, the solubility of the nonionic surfactant in the water phase and the solubility of the nonionic surfactant in the oil phase should be somewhat similar. Because tap water is normally added to the oil-based cleansing composition of the present invention, it is very difficult to adjust the solubility. Thus, the correlation between the oil phase and the nonionic surfactant is inevitably very important.

The present inventors have investigated the relationship between the IOB of the oil component and the optimum HLB of the nonionic surfactant. The results are shown in Tables 2 to 4.

TABLE 2

| Test example | 2-1 | 2-2 | 2-3 | 2-4 | 2-5 | 2-6 | 2-7 |
|---|---|---|---|---|---|---|---|
| Ion exchange water | 1 | 1 | 1 | 1 | 1 | 1 | 1 |
| Liquid paraffin | 59 | 49 | 39 | 29 | 19 | 9 | 0 |
| Cetyl isooctanoate | 0 | 10 | 20 | 30 | 40 | 50 | 59 |
| IOB | 0 | 0.022 | 0.043 | 0.065 | 0.087 | 0.108 | 0.128 |
| POE(6) glyceryl monoisostearate (HLB; 8) | 40 | 40 | 40 | 40 | 40 | 40 | 40 |
| Phase state when water is interfused | ○ | ○ | ○ | ○ | x | x | x |
| Transparency test when water is interfused | Δ | ○ | ○ | ○ | Δ | x | x |
| Sense of use when water is interfused | x | ○ | ○ | ○ | Δ | x | x |
| Cleansing performance when water is interfused | x | ○ | ○ | ○ | Δ | x | x |

TABLE 3

| Test example | 3-1 | 3-2 | 3-3 | 3-4 | 3-5 | 3-6 | 3-7 |
|---|---|---|---|---|---|---|---|
| Ion exchange water | 1 | 1 | 1 | 1 | 1 | 1 | 1 |
| Liquid paraffin | 59 | 49 | 39 | 29 | 19 | 9 | 0 |
| Cetyl isooctanoate | 0 | 10 | 20 | 30 | 40 | 50 | 59 |
| IOB | 0 | 0.022 | 0.043 | 0.065 | 0.087 | 0.108 | 0.128 |
| POE(8) glyceryl monoisostearate (HLB; 9) | 40 | 40 | 40 | 40 | 40 | 40 | 40 |
| Phase state when water is interfused | ○ | ○ | ○ | ○ | ○ | x | x |
| Transparency test when water is interfused | Δ | ○ | ○ | ○ | Δ | x | x |
| Sense of use when water is interfused | x | ○ | ○ | ○ | Δ | x | x |
| Cleansing performance when water is interfused | x | ○ | ○ | ○ | Δ | x | x |

TABLE 4

| Test example | 4-1 | 4-2 | 4-3 | 4-4 | 4-5 | 4-6 | 4-7 |
|---|---|---|---|---|---|---|---|
| Ion exchange water | 1 | 1 | 1 | 1 | 1 | 1 | 1 |
| Liquid paraffin | 59 | 49 | 39 | 29 | 19 | 9 | 0 |
| Cetyl isooctanoate | 0 | 10 | 20 | 30 | 40 | 50 | 59 |
| IOB | 0 | 0.022 | 0.043 | 0.065 | 0.087 | 0.108 | 0.128 |
| POE(10) glyceryl monoisostearate (HLB; 10) | 40 | 40 | 40 | 40 | 40 | 40 | 40 |
| Phase state when water is interfused | x | ○ | ○ | ○ | ○ | x | x |
| Transparency test when water is interfused | Δ | ○ | ○ | ○ | Δ | x | x |
| Sense of use when water is interfused | x | ○ | ○ | ○ | Δ | x | x |
| Cleansing performance when water is interfused | x | ○ | ○ | ○ | Δ | x | x |

As shown above, the desirable IOB of the oil component has a trend to increase with an increase of the HLB of the nonionic surfactant. In the region where the HLB of the nonionic surfactant is 8 to 10, it is preferable that the IOB of the oil component is 0.02 to 0.07.

When other hydrocarbon oils and ester oils are used, similar results to the above-described results were also obtained if the average IOB of the mixed oil is matched with the above IOB.

Example 2 and Comparative Examples 3 and 4

The cleansing compositions were prepared according to the formulations shown in Table 2. It was confirmed that, when water is interfused, a bicontinuous microemulsion phase (D) was formed in Example 2, and other phases were formed in Comparative Examples 3 and 4.

The compositions were evaluated based on the above-described criteria. The results are shown in Table 5.

TABLE 5

| Component | Exam. 2 | Comparative Exam. 3 | Comparative Exam. 4 |
|---|---|---|---|
| Ion exchange water | 4 | 4 | 4 |
| POE(8) glyceryl monoisostearate (HLB; 9) | 64 | 30 | 74 |
| Decamethylcyclopentasiloxane | 16 | 33 | 11 |
| Cetyl isooctanoate | 16 | 33 | 11 |

TABLE 5-continued

| Component | Exam. 2 | Comparative Exam. 3 | Comparative Exam. 4 |
|---|---|---|---|
| Phase state when water is interfused | ○ | x (W/O emulsion) | x (liquid crystal) |
| Transparency test when water is interfused | ○ | Δ | x |
| Viscosity (mPa·s) when water is interfused | 800 | 100 | 14000 |
| Cleansing performance when water is interfused | ○ | x | Δ |
| Eye irritation | ○ | ○ | ○ |

In reality, it is unlikely to supply a cleansing composition that is based on silicone oil. Therefore, the present inventors added silicone oil to the oil component that is based on hydrocarbon oil and ester oil in order to improve the cleansing performance especially for the makeup containing a silicone resin. The results are shown in Table 6.

TABLE 6

| Test example | 6-1 | 6-2 | 6-3 | 6-4 | 6-5 | 6-6 | 6-7 |
|---|---|---|---|---|---|---|---|
| Ion exchange water | 1 | 1 | 1 | 1 | 1 | 1 | 1 |
| Oil phase | 59 | 58 | 57 | 54 | 49 | 39 | 19 |
| POE(6) glyceryl monoisostearate (HLB; 9) | 40 | 40 | 40 | 40 | 40 | 40 | 40 |
| Decamethylcyclopentasiloxane | 0 | 1 | 2 | 5 | 10 | 20 | 40 |
| Phase state when water is interfused | ○ | ○ | ○ | ○ | ○ | x | x |
| Transparency test when water is interfused | Δ | ○ | ○ | ○ | Δ | x | x |
| Sense of use when water is interfused | x | ○ | ○ | ○ | Δ | Δ | Δ |
| Cleansing performance when water is interfused | x | ○ | ○ | ○ | Δ | x | x |

Mixed oil of liquid paraffin and cetyl isooctanoate in the ratio of 2:1 was used as the oil phase.

As is evident from Table 6, when 1 to 10% by mass of the silicone oil (decamethylcyclopentasiloxane) was added to the mixed oil, the excellent cleansing performance could be achieved while the suitable transparency and feeling in use were maintained.

Examples 3 to 5 and Comparative Examples 5 to 9

The cleansing compositions were prepared according to the formulations shown in Tables 7 to 9. The obtained cleansing compositions were evaluated based on the above-described criteria, and the results are also shown in Tables 7 to 9.

TABLE 7

| Component | Exam. 3 | Comparative Exam. 5 | Comparative Exam. 6 |
|---|---|---|---|
| Ion exchange water | 1 | 1 | 1 |
| POE(10) monoisostearate (HLB; 10) | 32 | — | — |
| POE(8) monolaurate (HLB; 11) | — | 32 | — |
| POE(3) monoisostearate (HLB; 5) | — | — | 32 |
| Myristyl isooctanoate | 67 | 67 | 67 |
| HLB of the surfactant | 10 | 11 | 5 |
| Phase state when water is interfused | ○ | ○ | x |

TABLE 7-continued

| Component | Exam. 3 | Comparative Exam. 5 | Comparative Exam. 6 |
|---|---|---|---|
| Transparency test when water is interfused | ○ | ○ | x |
| Viscosity (mPa·s) when water is interfused | 6500 | 3000 | 8000 |
| Cleansing performance when water is interfused | ○ | ○ | x |
| Eye irritation | ○ | Δ | ○ |

TABLE 8

| Component | Exam. 4 | Comparative Exam. 7 |
|---|---|---|
| Ion exchange water | 4 | 4 |
| EDTA-3Na·H₂O | 0.01 | 0.01 |
| Citric acid | 0.001 | 0.001 |
| Sodium citrate | 0.009 | 0.009 |
| Glycerin | 1 | 1 |
| Polyethylene glycol(12) diisostearate (HLB; 7) | 35 | — |
| Polyethylene glycol(6) diisostearate (HLB; 4) | — | 35 |
| Liquid paraffin | 37.79 | 37.79 |
| Glyceryl tri-2-ethylhexanoate | 5 | 5 |
| Isoparaffin | 5 | 5 |
| Dimetylsiloxane(6cs) | 3 | 3 |
| Stearyl alcohol | 0.1 | 0.1 |
| Pentaerythritol tetra-2-ethylhexanoate | 3 | 3 |
| Squalane | 3 | 3 |
| Metylphenyl polysiloxane | 3 | 3 |
| Ascorbic acid 2-glucoside | 0.1 | 0.1 |
| HLB of the surfactant | 7 | 4 |
| Phase state when water is interfused | ○ | x (W/O emulsion) |
| Transparency test when water is interfused | ○ | x |
| Viscosity (mPa·s) when water is interfused | 1200 | 500 |
| Cleansing performance when water is interfused | ○ | x |
| Eye irritation | ○ | ○ |

TABLE 9

| Component | Exam. 5 | Comparative Exam. 8 | Comparative Exam. 9 |
|---|---|---|---|
| Ion exchange water | 3 | 3 | 3 |
| Sorbitan isostearate (HLB; 9) | 30 | 30 | 30 |
| Isostearyl alcohol | 4 | — | — |
| Isostearic acid | — | 4 | — |
| Liquid paraffin | 31.4 | 31.4 | 33.4 |
| Cetyl isooctanoate | 31.4 | 31.4 | 33.4 |
| *Phellodendron* bark extracts | 0.1 | 0.1 | 0.1 |
| HLB of the surfactant | 9 | 9 | 9 |
| Phase state when water is interfused | ○ | ○ | x |
| Transparency test when water is interfused | ○ | ○ | x |
| Viscosity (mPa·s) when water is interfused | 600 | 600 | 90 |
| Cleansing performance when water is interfused | ○ | ○ | Δ |
| Eye irritation | ○ | ○ | ○ |

What is claimed is:

1. An oil-based cleansing composition comprising (A) a nonionic surfactant having a HLB of 8 to 10, and (B) an oil component, the IOB of (B) said oil component is 0.02 to 0.07, and the mass ratio of component (A) and component (B) is 1:4 to 2:1, and said oil-based cleansing composition satisfies the following conditions (1) and (2):
   (1) the amount of water in the composition is less than 5% by mass, and
   (2) a micellar aqueous solution phase or a bicontinuous microemulsion phase is formed when said oil-based cleansing composition and water are mixed in the ratio of 4:6,
      wherein the micellar aqueous solution phase is optically isotropic exhibiting a clear to slightly blue, translucent appearance, and the bicontinuous microemulsion phase is optically isotropic exhibiting a transparent appearance.

2. An oil-based cleansing composition comprising (A) a nonionic surfactant having a HLB of 8 to 10, and (B) an oil component, and said IOB of (B) said oil component is 0.02 to 0.07, and the mass ratio of component (A) and component (B) is 1:4 to 2:1, and said oil-based cleansing composition satisfies the following conditions (1) and (2):
   (1) the amount of water in the composition is less than 5% by mass, and
   (2) a micellar aqueous solution phase or a bicontinuous microemulsion phase is formed when said oil-based cleansing composition and water are mixed in the ratio of 4:6,
      wherein upon mixing the oil-based cleansing composition and water in the ratio of 4:6, a bicontinuous microemulsion phase is formed which is optically isotropic exhibiting a transparent appearance.

3. The oil-based cleansing composition according to claim 1, wherein the alkyl chain length in (A) said nonionic surfactant is not less than 16 on the average.

4. The oil-based cleansing composition according to claim 1, wherein (B) said oil component contains not less than 80% of hydrocarbon oil and/or ester oil.

5. The oil-based cleansing composition according to claim 1, wherein (B) said oil component further contains 1 to 10% of silicone oil.

6. The oil-based cleansing composition of claim 1, further comprising (C) a liquid fatty acid or a liquid alcohol with the alkyl chain length of not less than 16 is further contained.

7. The oil-based cleansing composition according to claim 6, wherein the mass ratio of component (C) and component (A) is in the range of 1:40 to 1:3.

8. The oil-based cleansing composition according to claim 1, wherein the below-described condition (3) is satisfied in addition to conditions (1) and (2):
   (3) the viscosity measured with a B-type viscometer is not more than 10000 mPa·s when said oil-based cleansing composition and water is mixed in the mass ratio of 7:3.

9. The oil-based cleansing composition according to claim 3, wherein (B) said oil component contains not less than 80% of hydrocarbon oil and/or ester oil.

10. The oil-based cleansing composition according to claim 3, wherein (B) said oil component further contains 1 to 10% of silicone oil.

11. The oil-based cleansing composition of claim 5, wherein further comprising (C) a liquid fatty acid or a liquid alcohol with the alkyl chain length of not less than 16 is further contained.

* * * * *